(12) United States Patent
Dinino et al.

(10) Patent No.: US 11,259,840 B2
(45) Date of Patent: Mar. 1, 2022

(54) VALVE ASSEMBLIES FOR SURGICAL ACCESS ASSEMBLIES

(71) Applicant: Covidien LP, Mansfield, MA (US)

(72) Inventors: Matthew Dinino, Newington, CT (US); Roy Pilletere, North Haven, CT (US); Nicolette LaPierre, Windsor Locks, CT (US); George Matta, Plainville, MA (US); Jacob Baril, Norwalk, CT (US); Eric Brown, Haddam, CT (US); Garrett Ebersole, Hamden, CT (US); Kevin Desjardin, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 244 days.

(21) Appl. No.: 16/448,782

(22) Filed: Jun. 21, 2019

(65) Prior Publication Data

US 2020/0397473 A1 Dec. 24, 2020

(51) Int. Cl.
*A61B 17/34* (2006.01)

(52) U.S. Cl.
CPC ...... *A61B 17/3462* (2013.01); *A61B 17/3423* (2013.01); *A61B 17/3498* (2013.01)

(58) Field of Classification Search
CPC ............ A61B 17/3498; A61B 17/3423; A61B 17/3462; A61B 2017/3425–3427; A61B 2017/3464
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |

(Continued)

FOREIGN PATENT DOCUMENTS

| | | |
|---|---|---|
| CA | 2702419 A1 | 11/2010 |
| EP | 0226026 A2 | 6/1987 |

(Continued)

OTHER PUBLICATIONS

European Search Report dated Oct. 9, 2020, corresponding to counterpart European Application No. 20180529.8; 8 pages.

*Primary Examiner* — Diane D Yabut
*Assistant Examiner* — Brigid K Byrd
(74) *Attorney, Agent, or Firm* — Carter, DeLuca & Farrell LLP (57) ABSTRACT

Access assemblies include an instrument valve housing and a valve assembly. The valve assembly includes a guard assembly, a seal assembly disposed adjacent to the guard assembly, and a gimbal mount assembly supporting the guard assembly and the seal assembly. The gimbal mount assembly is configured to permit angulation of the valve assembly relative to the instrument valve housing.

20 Claims, 7 Drawing Sheets

(56) References Cited

U.S. PATENT DOCUMENTS

| | | |
|---|---|---|
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 * | 11/2002 | Racenet ............ F16K 15/147 604/167.06 |
| 6,485,410 B1 | 11/2002 | Loy |
| 6,488,620 B1 | 12/2002 | Segermark et al. |
| 6,488,692 B1 | 12/2002 | Spence et al. |

(56) References Cited

U.S. PATENT DOCUMENTS

| | | |
|---|---|---|
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,569,140 B1 | 5/2003 | Mizutani et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 2001/0037053 A1 | 11/2001 | Bonadio et al. |
| 2002/0055714 A1 | 5/2002 | Rothschild |

(56) References Cited

U.S. PATENT DOCUMENTS

| | | |
|---|---|---|
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224120 A1* | 10/2006 | Smith ............... A61M 39/0606 604/167.01 |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0081880 A1* | 4/2010 | Widenhouse ....... A61B 17/3423 600/201 |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0249711 A1* | 9/2010 | Fischvogt .......... A61B 17/3462 604/167.03 |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1 | 10/2011 | Albrecht et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |

(56) References Cited

U.S. PATENT DOCUMENTS

| | | |
|---|---|---|
| 2013/0245373 A1 | 9/2013 | Okoniewski |
| 2013/0274559 A1 | 10/2013 | Fowler et al. |
| 2013/0310651 A1 | 11/2013 | Alfieri |
| 2013/0310773 A1* | 11/2013 | Richard ............ A61B 17/3498 604/278 |
| 2014/0018632 A1 | 1/2014 | Kleyman |
| 2014/0235949 A1 | 8/2014 | Smith |
| 2015/0223833 A1 | 8/2015 | Coffeen et al. |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2014116889 A1 | 7/2014 |
| WO | 2016186905 A1 | 11/2016 |
| WO | 2018024103 A1 | 2/2018 |

* cited by examiner

VALVE ASSEMBLIES FOR SURGICAL ACCESS ASSEMBLIES

FIELD

The present disclosure relates to surgical access assemblies for minimally invasive surgery, including seals. More particularly, the present disclosure relates to valve assembles for surgical access assemblies.

BACKGROUND

In order to facilitate minimally invasive surgery, a working space may be created at the desired surgical site. An insufflation fluid, typically $CO_2$, is introduced into the abdomen of the patient to create an inflated state called a pneumoperitoneum. Surgical access assemblies are utilized to allow the introduction of surgical instrumentation and endoscopes (or other visualization tools) into the insufflated abdomen. These surgical access assemblies help maintain the insufflation pressure of the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable adjusting to instrumentation of multiple sizes and withstanding multiple insertions of surgical instrumentation. Some of the instrumentation can include sharp edges that can tear or otherwise damage seals. Therefore, it would be beneficial to have a surgical access assembly with improved seal durability.

SUMMARY

A surgical access assembly including a valve assembly is provided. The surgical access assembly includes an instrument valve housing and the valve assembly. The instrument valve housing includes upper and lower housing sections and defines a cavity therebetween. The upper housing section has an outward facing surface and the lower housing section has an inward facing surface. The surgical access assembly further includes a valve assembly disposed within the cavity of the instrument valve housing. The valve assembly includes a guard assembly, and a seal assembly disposed adjacent to the guard assembly. The seal assembly has a nonsolid inner circumference. The valve assembly further includes a gimbal mount assembly supporting the guard assembly and the seal assembly. The gimbal mount assembly includes an outer semispherical surface in operable engagement with the inward facing surface of the lower housing section and an inner surface in operable engagement with the outward facing surface of the upper housing section. The gimbal mount assembly is configured to permit angulation of the valve assembly relative to the instrument valve housing.

In embodiments, the gimbal mount assembly includes a gimbal base and a gimbal retainer. The gimbal base may include the outer semispherical surface and the gimbal retainer includes the inner surface. The gimbal base may define a recess, with the gimbal retainer being securely received within the recess. The guard assembly and the seal assembly may be disposed within the recess of the gimbal base. The gimbal base may include a shelf. The guard assembly and the seal assembly may be disposed between the shelf and the gimbal retainer. At least one of the gimbal retainer or the gimbal base may include a plurality of pins and the other of the gimbal retainer or the gimbal base may define a plurality of openings corresponding to the plurality of pins.

In another aspect, an instrument valve housing including upper and lower housing sections is provided. The upper housing section includes an outward facing surface and the lower housing section includes an inward facing surface. The upper and lower housing sections define a cavity therebetween. The instrument valve housing further includes a valve assembly operably disposed within the cavity of the instrument valve housing. The valve assembly includes a guard assembly, a seal assembly disposed adjacent to the guard assembly, and a gimbal mount assembly supporting the guard assembly and the seal assembly. The seal assembly has a nonsolid inner circumference. The gimbal mount assembly includes an outer semispherical surface in operable engagement with the inward facing surface of the lower housing section and an inner surface in operable engagement with the outward facing surface of the upper housing section. The gimbal mount assembly is configured to permit angulation of the valve assembly relative to the instrument valve housing.

In embodiments, the gimbal mount assembly includes a gimbal base and a gimbal retainer. The gimbal base may include the outer semispherical surface and the gimbal retainer includes the inner surface. The gimbal base may define a recess with the gimbal retainer being securely received within the recess. The guard assembly and the seal assembly may be disposed within the recess of the gimbal base. The gimbal base may include a shelf. The guard assembly and the seal assembly may be disposed between the shelf and the gimbal retainer. At least one of the gimbal retainer or the gimbal base may include a plurality of pins and the other of the gimbal retainer or the gimbal base may define a plurality of openings corresponding to the plurality of pins. The seal assembly may include four seal sections.

Also provided is a valve assembly including a guard assembly and a seal assembly disposed adjacent to the guard assembly. The seal assembly has a nonsolid inner circumference. The valve assembly further includes a gimbal mount assembly supporting the guard assembly and the seal assembly. The gimbal mount assembly includes an outer semispherical surface in operable engagement with an inner surface of a lower housing section of an instrument valve housing and an inner surface in operable engagement with an outward facing surface of an upper housing section of the instrument valve housing. The gimbal mount assembly is configured to permit angulation of the valve assembly relative to the instrument valve housing.

In embodiments, the gimbal mount assembly includes a gimbal base and a gimbal retainer. The gimbal base may include the outer semispherical surface and the gimbal retainer includes the inner surface. The gimbal base may define a recess with the gimbal retainer being securely received within the recess.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Particular embodiments of the present surgical access assemblies and valve assemblies are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Surgical access assemblies with obturators are employed during minimally invasive surgery, e.g., laparoscopic surgery, and provide for the sealed access of surgical instruments into an insufflated body cavity, such as the abdominal cavity. The surgical access assemblies of the present disclosure include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the surgical access assembly can be introduced into the abdomen. The handle of the obturator can engage or selectively lock into the instrument valve housing of the surgical access assembly.

Surgical access assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument valve housing of the surgical access assembly includes valves that prevent the escape of insufflation fluid from the body cavity, while also allowing surgical instruments to be inserted into the cavity.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplary trocar obturators and exemplary cannulas, please refer to commonly owned PCT Publication No. WO 2016/186905 ("the '905 publication"), the content of which is hereby incorporated by reference herein in its entirety.

Figures 1, 2:
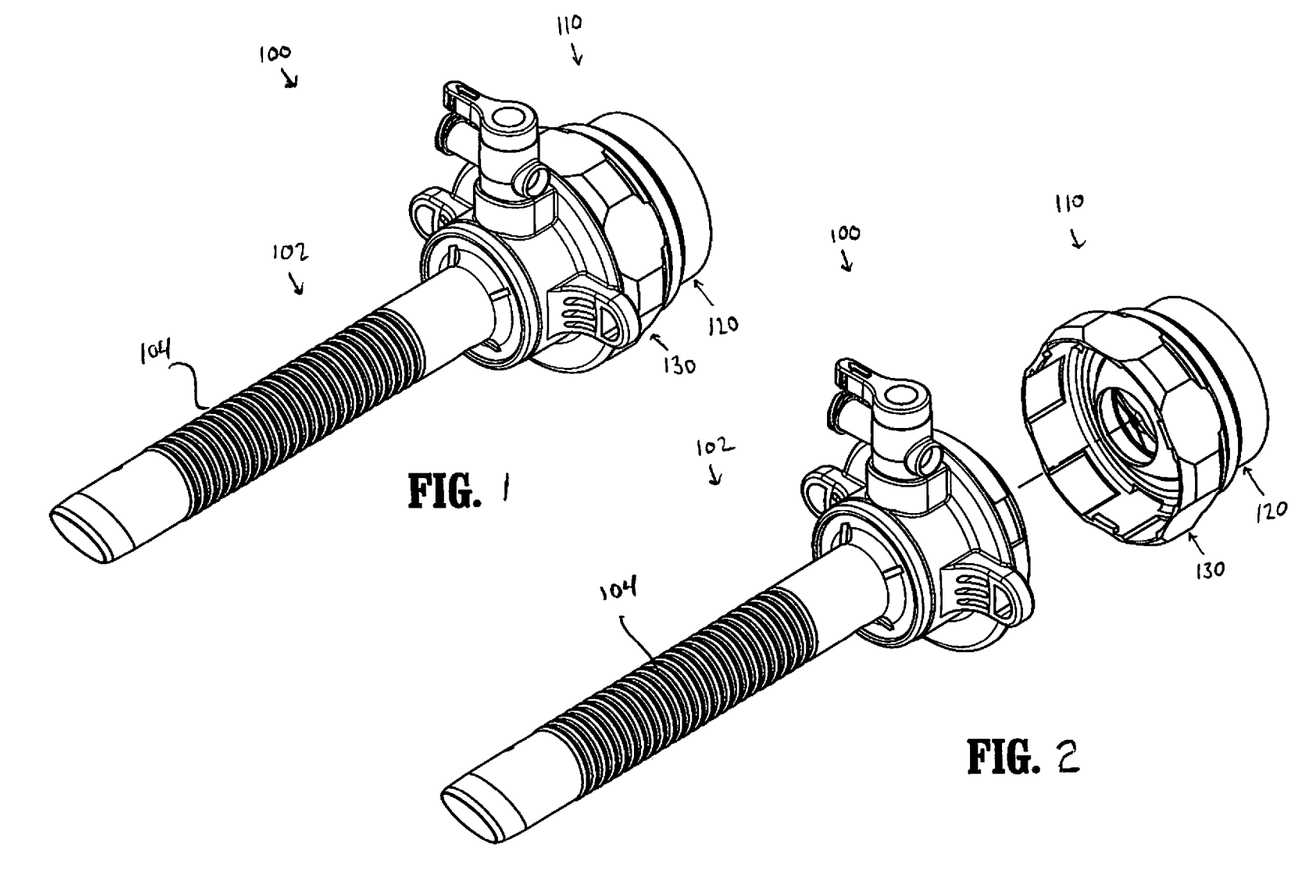
FIG. 1 is a side perspective view of a surgical access assembly according to an embodiment of the present disclosure.
FIG. 2 a side perspective view of the surgical access assembly shown in FIG. 1, with an instrument valve assembly separated from a cannula assembly.

With initial reference to FIG. 1, an access assembly according to aspects of the present disclosure is shown generally as surgical access assembly 100. The surgical access assembly 100 includes a cannula 102 and an instrument valve housing 110 releasably secured to the cannula 102. For a detailed description of an exemplary surgical access assembly, please refer to the '905 publication.

Figure 3:
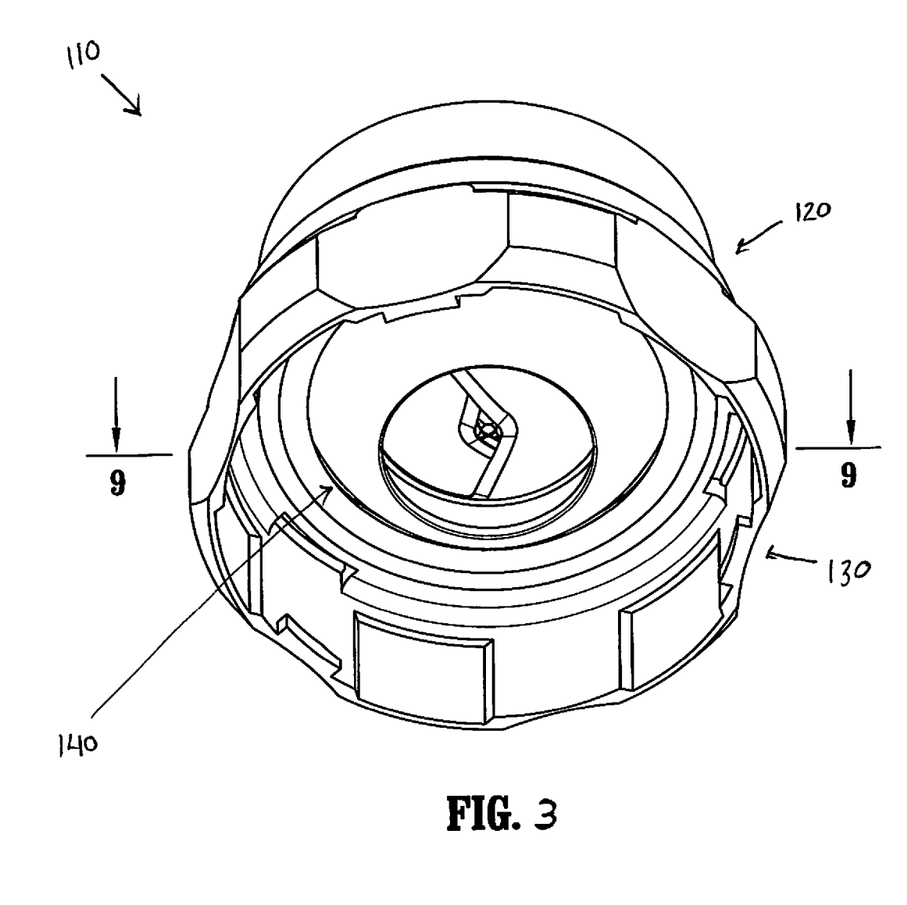
FIG. 3 is a bottom perspective view of the instrument valve assembly shown in FIG. 2.

With reference now to FIGS. 2 and 3, the instrument valve housing 110 of the surgical access assembly 100 includes an upper housing section 120 and a lower housing section 130. The instrument valve housing 110 is configured to support a gimbal valve assembly 140. More particularly, the upper housing section 120 is secured to the lower housing section 130, and the gimbal valve assembly 140 is operably received between the upper and lower housing sections 120, 130. The lower housing section 130 may be releasably or permanently attached to a cannula tube 104 (FIG. 1) of the surgical access assembly 102. In embodiments, either or both of the upper and lower housing sections 120, 130 of the instrument valve housing 110 include knurls, indentations, tabs, or be otherwise configured to facilitate engagement by a clinician.

The surgical access assembly 100 may also include features for the stabilization of the surgical access assembly 100. For example, a distal portion of a cannula tube 104 may carry a balloon anchor or another expandable member that engages the abdomen from the interior side. See, for example, U.S. Pat. No. 7,300,448, the entire disclosure of which is hereby incorporated by reference herein. A feature on the opposite side of the abdominal wall may be used to further stabilize the surgical access assembly, such as adhesive tabs or adjustable foam collars.

Figure 9:
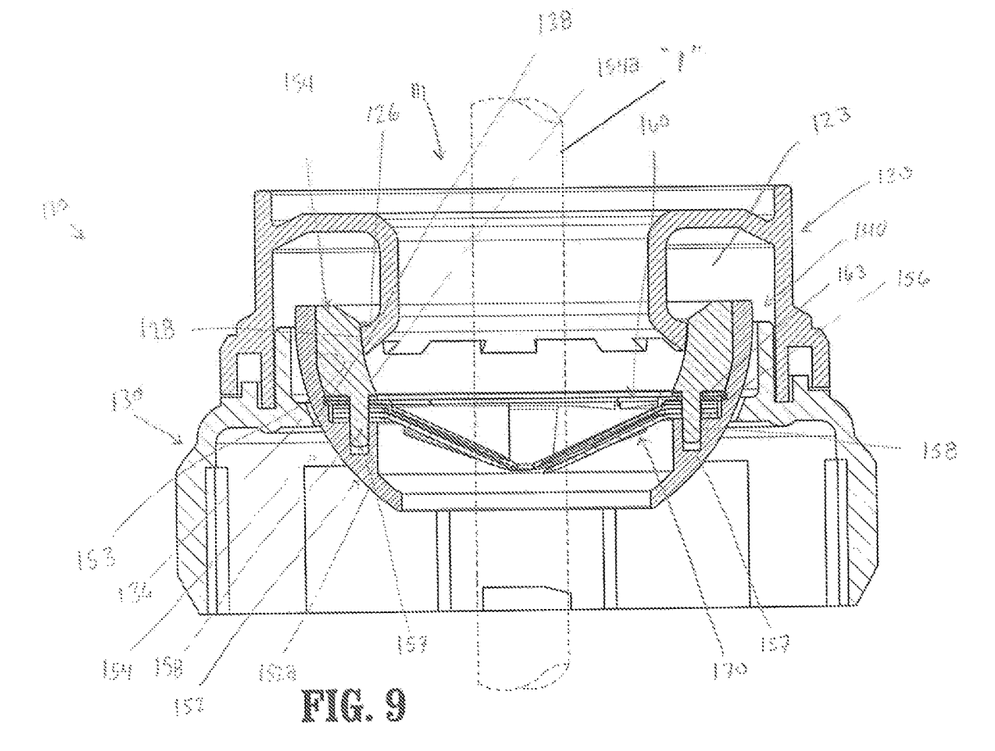
FIG. 9 is a side cross-sectional view of the instrument valve assembly shown in FIG. 3 taken along section line 9-9 shown in FIG. 3.

The upper and lower housing sections 120, 130 of the instrument valve housing 110 define a longitudinal passage 111 (FIG. 9) for receipt of a surgical instrument "I" (FIG. 9). The gimbal valve assembly 140 is supported within the instrument valve housing 110 to provide sealed passage of the surgical instrument "I" through the surgical access assembly 100.

Figure 4:
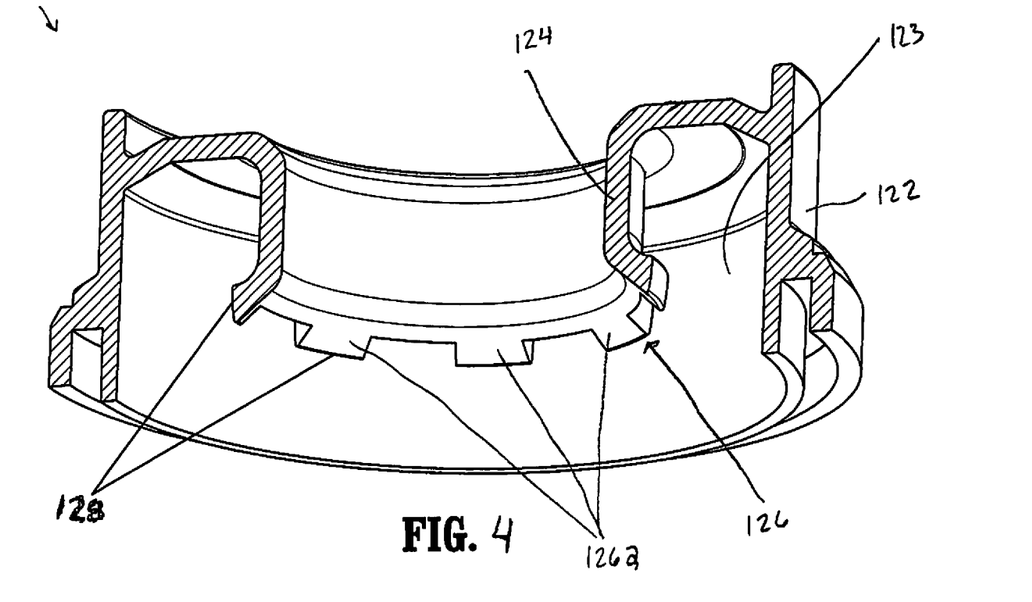
FIG. 4 is a side cross-sectional view of a upper housing section of the instrument valve assembly shown in FIG. 3, taken along section line 4-4 shown in FIG. 6.

With particular reference to FIG. 4, the upper housing section 120 of the instrument valve housing 110 (FIG. 1) of the surgical access assembly 100 includes an outer annular portion 122 and an inner annular portion 124, and defines a cavity 123 (FIG. 9) between the first and outer annular portions 122, 124. A flange portion 126 extends radially outward and in a longitudinal direction from a free end of the inner annular portion 124. The flange portion 126 may be formed of spaced segments 126a (as shown), or may form a continuous ring. The flange portion 126 includes an outwardly facing surface 128. The outwardly facing surface 128 provides an upper support for the gimbal valve assembly 140. In embodiments, and as shown, the outwardly facing surface 128 is curved to accommodate the semispherical inner surface 152a of the gimbal retainer 154, and facilitates sealing between the surfaces 128, 154a.

Figure 5:
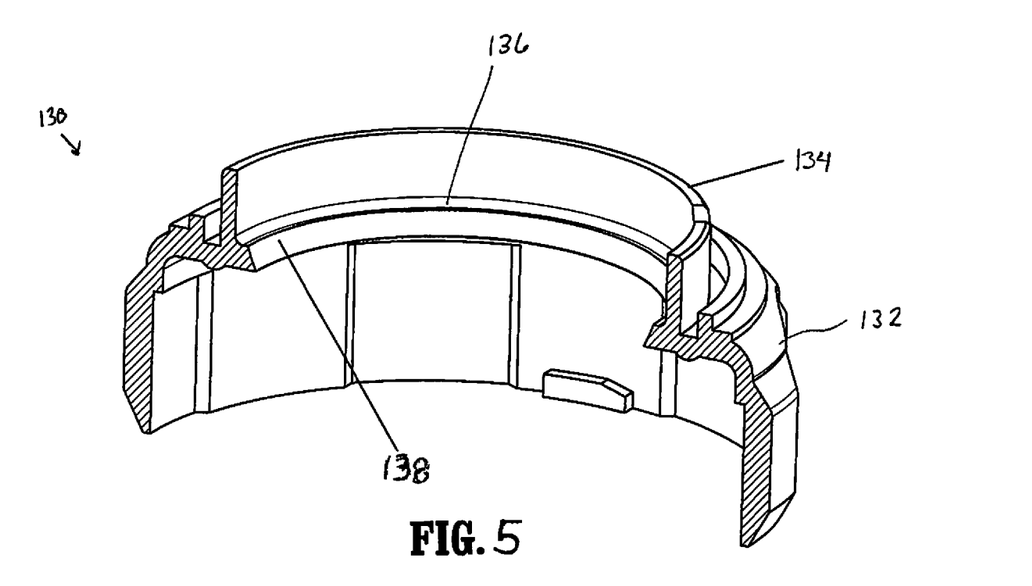
FIG. 5 is a side cross-sectional view of a lower housing section of the instrument valve assembly shown in FIG. 3, taken along section line 5-5 shown in FIG. 6.

Turning to FIG. 5, the lower housing section 130 of the instrument valve housing 110 of the surgical access assembly 100 includes an annular base portion 132, an annular extension portion 134 extending from the base portion 132, and a lip portion 136 extending radially inward from the annular extension portion 134. The lip portion 136 includes an inwardly facing surface 138. The inwardly facing surface 138 of the lip portion 136 provides a lower support for the gimbal valve assembly 140. The inwardly facing surface 138 of the lip portion 136, in combination with the outwardly facing surface 128 of the flange portion 126 of the upper housing section 120, operably support the gimbal valve assembly 140. In embodiments, and as shown, the inwardly facing surface 138 is curved to accommodate the curved outer surface 152a of the gimbal base 152, and facilitates sealing between the surfaces 138, 152a (see FIG. 9).

Figure 6:
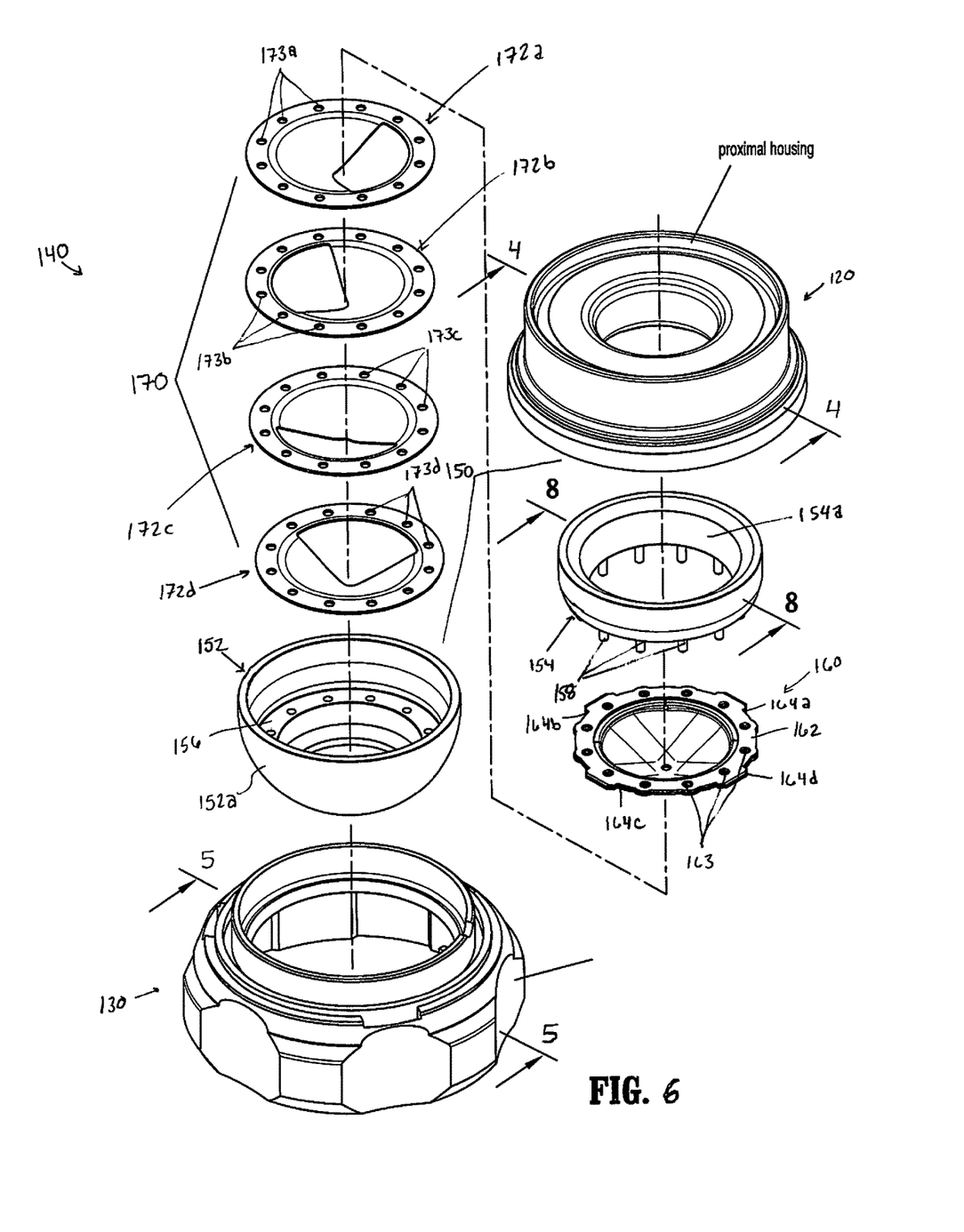
FIG. 6 is an exploded perspective view of the instrument valve assembly shown in FIG. 4, including a gimbal valve assembly, with parts separated.

With particular reference now to FIG. 6, the gimbal valve assembly 140 of the surgical access assembly 100 includes a gimbal mount assembly 150, a guard assembly 160, and a seal assembly 170. The gimbal mount assembly 150 of the gimbal valve assembly 140 permits radial movement of the gimbal valve assembly 140 within the instrument valve housing 110 when a surgical instrument "I" (FIG. 9) is received through the gimbal valve assembly 140. The guard assembly 160 protects the seal assembly 170 during insertion and withdrawal of the surgical instrument "I" through the seal assembly 170. The seal assembly 170 provides sealed passage of the surgical instrument "I" through the instrument valve housing 110.

In embodiments, a bellows may be secured to the gimbal valve assembly 140 for biasing the gimbal valve assembly 140 to a generally centered position while the surgical instrument "I" is received therethrough and for maintaining the gimbal valve assembly 140 in a generally centered position once the surgical instrument "I" is withdrawn from within the instrument valve housing 110. For a detailed description of an exemplary gimbal assembly including a bellows, please refer to U.S. Pat. App. Pub. No. 2013/0310773, the content of which is incorporated herein by reference in its entirety.

Still referring to FIG. 6, the gimbal mount assembly 150 includes a gimbal base 152 and a gimbal retainer 154. The gimbal base 152 and the gimbal retainer 154 operate together to support the guard assembly 160 and the seal assembly 170. The gimbal mount assembly 150 is operably supported between the upper housing section 120 and the lower housing section 130.

Figure 7:
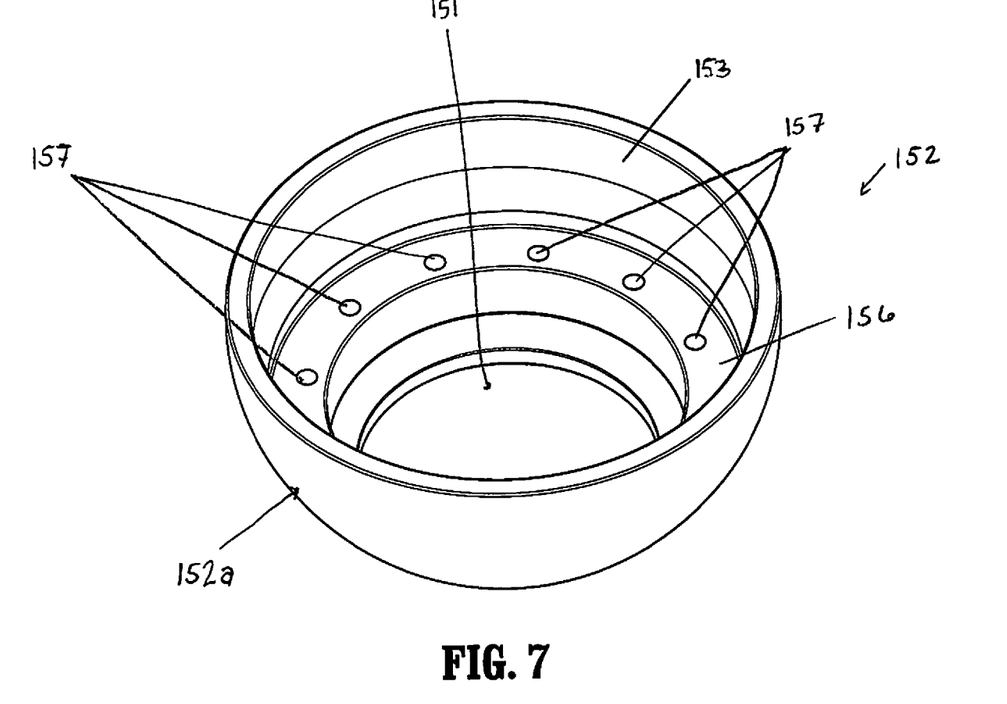
FIG. 7 is a side perspective view of a gimbal base of a gimbal retainer of the gimbal valve assembly shown in FIG. 3.

With additional reference to FIG. 7, the gimbal base 152 of the gimbal mount assembly 150 includes a semispherical body having a semispherical outer surface 152a. The semispherical outer surface 152a is configured to be supported by the inwardly facing surface 138 of the lip portion 136 of the lower housing section 130 of the instrument valve housing 110. The gimbal base 152 defines a central opening 151 through which surgical instruments "I" (FIG. 9) may be received. The gimbal base 152 includes a shelf 156 and defines an annular recess 153 proximal of the shelf 156. The annular recess 153 in the gimbal base 152 is configured to receive the gimbal retainer 154. The shelf 156 defines a plurality of openings 157 for receiving a plurality of pins 158 of the gimbal retainer 154 that are configured to secure the gimbal retainer 154 to the gimbal base 152 and to maintain the gimbal retainer 154, the guard assembly 160, and seal assembly 170 within the annular recess 153 in the gimbal base 152.

Figure 8:
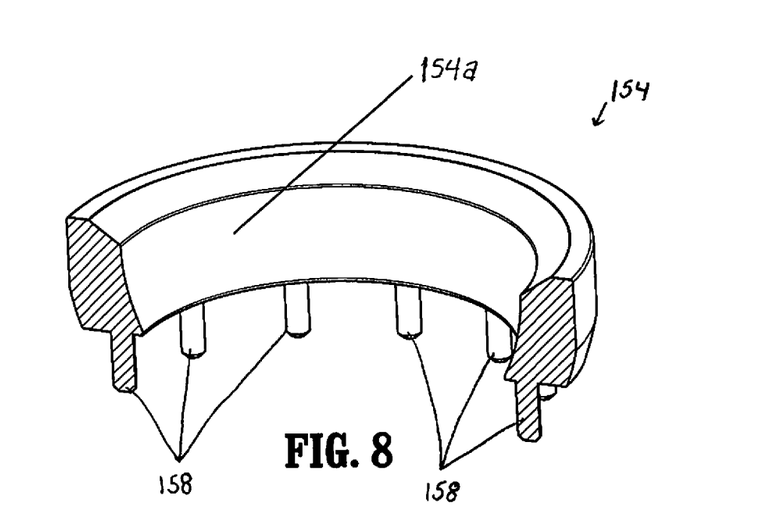
FIG. 8 is a perspective cross-sectional view of a gimbal retainer of the gimbal valve assembly shown in FIG. 3, taken along section line 8-8 shown in FIG. 6.

Turning to FIG. 8, the gimbal retainer 154 of the gimbal mount assembly 150 includes a substantially annular body having a curved inner surface 154a. The curved inner surface 154a is configured to be engaged by the outwardly facing surface 128 of the flange portion 126 of the upper housing section 120 of the instrument valve housing 110. The plurality of pins 158 extending from the gimbal retainer 154 are configured to be received within the plurality of openings 157 in the shelf 156 of the gimbal base 152.

With reference back to FIG. 6, the guard assembly 160 of the valve assembly 140 is configured to protect the seal assembly 170 during insertion and removal of the surgical instrument "I" (FIG. 9) passing through the instrument valve housing 110. The guard assembly 160 includes a ring portion 162 and first, second, third, and fourth petals 164a-d. The guard assembly 160 may be formed from a sheet of plastic/polymeric material by stamping with a tool that forms the ring portion 162 and the first, second, third, and fourth petals 164a-d. Alternatively, the guard assembly 160 may be formed by molding or other techniques. The ring portion 162 of the guard assembly 160 defines a plurality of openings 163 configured to receive the plurality of pins 158 of the gimbal retainer 154 of the gimbal mount assembly 150.

It is envisioned that the guard assembly may include any number of petals, and the petals may include flap portions of any size or configuration. See, for example, U.S. Pat. Nos. 5,895,377 and 6,569,140, the contents of which are incorporated herein by reference in its entirety.

With reference still to FIG. 6, the seal assembly 170 of the valve assembly 140 is configured to provide a seal around an outer surface of the surgical instrument "I" (FIG. 9) passing through the instrument valve housing 110. In embodiments, and as shown, the seal assembly 170 includes first, second, third, and fourth seal sections 172a-d. The multi-section seal configuration provides a non-solid inner circumference seal, e.g., non-continuous inner circumference. Having a non-solid inner circumference reduces the likelihood of tearing during insertion and withdrawn of surgical instruments "I" (FIG. 9). Although shown including four independent seal sections, it is envisioned that any seal assembly that includes a non-solid inner circumference seal is suitable for use with the aspects of the present disclosure.

The first, second, third, and fourth seal section 172a-d of the seal assembly 170 may be formed of an elastic material, e.g., rubber, polyisoprenes, or silicone elastomers, and may include one or more fabric layers. Each of the first, second, third, and fourth seal section 172a-d of the seal assembly 170 defines a plurality of openings 173a-d. The plurality of openings 173a-d receive pins 158 (FIG. 6) of the gimbal retainer 154 to maintain the seal assembly 170 in the folded condition and to secure the seal assembly 170 relative to the guard assembly 160 and the gimbal mount assembly 150.

With particular reference to FIG. 9, the gimbal valve assembly 140 of the surgical access assembly 100 is supported within the instrument valve housing 110. The gimbal valve assembly 140 includes a guard assembly 160 and a seal assembly 170 secured within the annular recess 153 defined by the gimbal base 152 of the gimbal mount assembly 150 by the gimbal retainer 154. More particularly, the seal assembly 170 is disposed adjacent the shelf 156 of the gimbal base 152, and the guard assembly 160 is disposed between the seal assembly 170 and the gimbal retainer 154. The plurality of pins 158 of the gimbal retainer 154 extend through the plurality of openings 163 in the guard assembly 160, through the plurality of openings 173*a-d* (FIG. 6) in the seal assembly 170, and into the plurality of openings 157 in the shelf 156 of the gimbal base 152. Although shown with the plurality of pins 158 extending from the gimbal retainer 154 of the gimbal mount assembly 150, the plurality of pins may instead extend from the gimbal base 152 and/or from both the gimbal base 152 and the gimbal housing 154. The plurality of pins 158 may be retained within the plurality of openings 157 using adhesive, friction fit, fasteners, or in any suitable manner.

With continued reference to FIG. 9, the gimbal valve assembly 140 of the surgical access assembly 100 is supported between the upper and lower housing sections 120, 130 of the instrument valve housing 110. The gimbal valve assembly 140 is supported between the outward facing surface 128 of the flange portion 126 of the upper housing section 120 of the instrument valve housing 110 and the inward facing surface 138 of the lip portion 136 of the lower housing section 130. More particularly, the curved inner surface 154*a* of the gimbal retainer 154 of the gimbal mount assembly 150 engages the outwardly facing surface 128 of the flange portion 126 of the upper housing section 120 and the semispherical outer surface 152*a* of the gimbal base 152 engages the inward facing surface 138 of the lip portion 136 of the lower housing section 130. Any or all of the contact surfaces may be coated or otherwise formed of a reduced friction material to permit movement of the gimbal mount assembly 150 relative to the instrument valve housing 110, and/or to facilitate sealing between the surfaces. In addition, or alternatively, a lubricant or other friction reducing substance may be added to one or more of the surfaces to facilitate movement of the gimbal mount assembly 140. In addition, or alternatively, a sealant or other sealing substance may be added to one or more of the surfaces to facilitate sealing between the instrument valve housing 110 and the instrument valve assembly 120.

Figure 10:
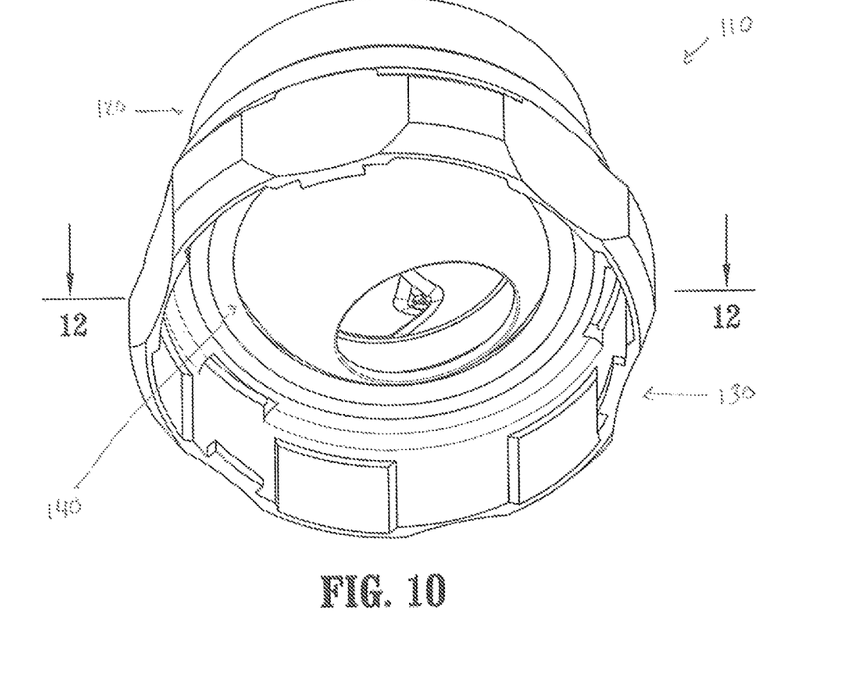
FIG. 10 is a bottom perspective view of the instrument valve assembly shown in FIG. 3, with the gimbal valve assembly in a non-centered position.
Figure 11:
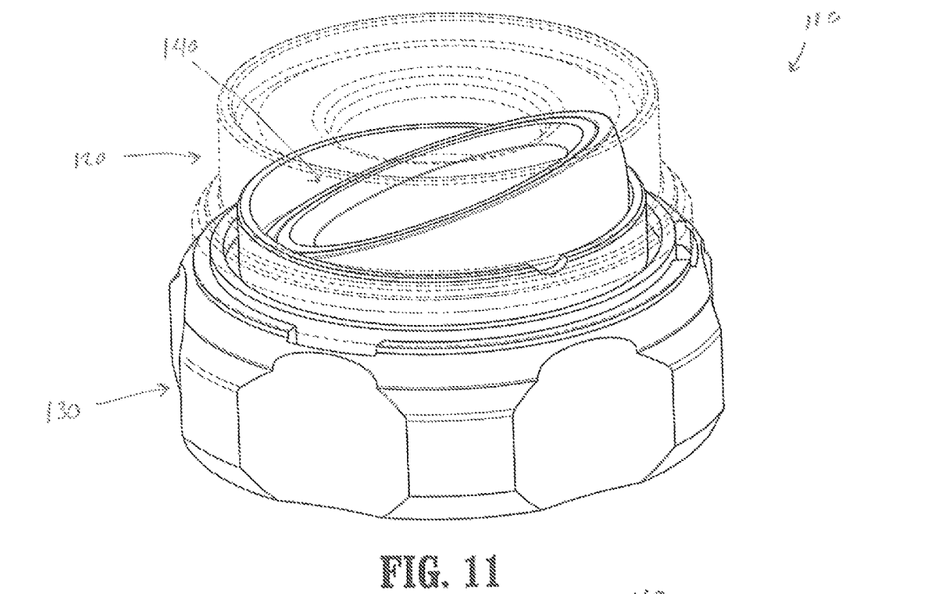
FIG. 11 is a side perspective view of the instrument valve assembly as shown in FIG. 10.
Figure 12:
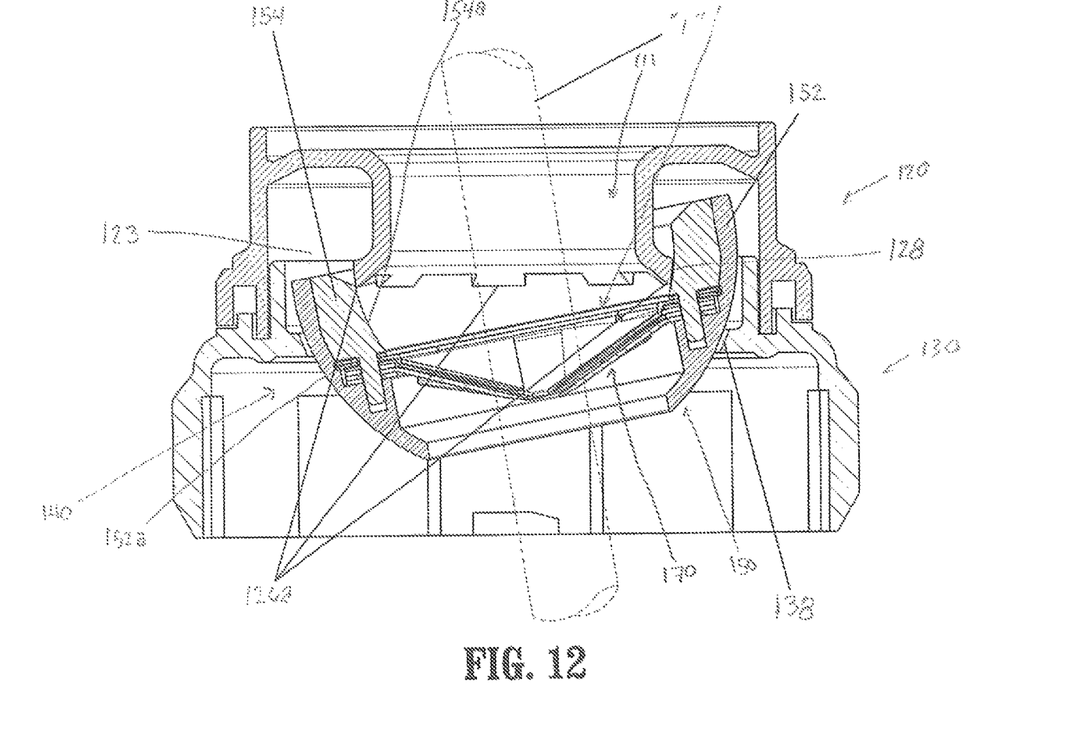
FIG. 12 is a side cross-sectional view of the instrument valve assembly as shown in FIG. 10, taken along section line 12-12 of FIG. 10.

With reference to FIGS. 10-12, the instrument valve housing 110 and the gimbal mount assembly 150 are configured to permit angulation of the surgical instrument "I" received through the gimbal valve assembly 140. In embodiments, and as shown, gimbal mount assembly 150 permits angulation of the surgical instrument "I" through three-hundred sixty degrees of angulation.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical access assembly comprising:
   an instrument valve housing including upper and lower housing sections defining a cavity, the upper housing section having an outward facing surface and the lower housing section having an inward facing surface; and
   a valve assembly disposed within the cavity of the instrument valve housing, the valve assembly defining a longitudinal axis and including:
      a guard assembly;
      a seal assembly disposed adjacent to the guard assembly, the seal assembly having a plurality of seal sections arranged circumferentially around the longitudinal axis collectively forming an aperture having a non-continuous circumference; and
      a gimbal mount assembly supporting the guard assembly and the seal assembly, the gimbal mount assembly including an outer semispherical surface in operable engagement with the inward facing surface of the lower housing section and an inner surface in operable engagement with the outward facing surface of the upper housing section, wherein the gimbal mount assembly is configured to permit angulation of the valve assembly relative to the instrument valve housing.

2. The surgical access assembly of claim 1, wherein the gimbal mount assembly includes a gimbal base and a gimbal retainer.

3. The surgical access assembly of claim 2, wherein the gimbal base includes the outer semispherical surface and the gimbal retainer includes the inner surface.

4. The surgical access assembly of claim 3, wherein the gimbal base defines a recess, the gimbal retainer being securely received within the recess.

5. The surgical access assembly of claim 4, wherein the guard assembly and the seal assembly are disposed within the recess of the gimbal base.

6. The surgical access assembly of claim 4, wherein the gimbal base includes a shelf, the guard assembly and the seal assembly being disposed between the shelf and the gimbal retainer.

7. The surgical access assembly of claim 6, wherein at least one of the gimbal retainer or gimbal base includes a plurality of pins and the other of the gimbal retainer or the gimbal base defines a plurality of openings corresponding to the plurality of pins.

8. An instrument valve housing comprising:
   an upper housing section including an outward facing surface;
   a lower housing section including an inward facing surface, the upper and lower housing sections defining a cavity therebetween; and
   a valve assembly operably disposed within the cavity, the valve assembly defining a longitudinal axis and including:
      a guard assembly;
      a seal assembly disposed adjacent to the guard assembly, the seal assembly having a plurality of seal sections arranged circumferentially around the longitudinal axis collectively forming an aperture having a non-continuous circumference; and
      a gimbal mount assembly supporting the guard assembly and the seal assembly, the gimbal mount assembly including an outer semispherical surface in operable engagement with the inward facing surface of the lower housing section and an inner surface in operable engagement with the outward facing surface of the upper housing section, wherein the gimbal mount assembly is configured to permit angulation of the valve assembly relative to the instrument valve housing.

9. The instrument valve housing of claim 8, wherein the gimbal mount assembly includes a gimbal base and a gimbal retainer.

10. The instrument valve housing assembly of claim 9, wherein the gimbal base includes the semispherical outer surface and the gimbal retainer includes the inner surface.

11. The instrument valve housing of claim 10, wherein the gimbal base defines a recess, the gimbal retainer being securely received within the recess.

12. The instrument valve housing of claim 11, wherein the guard assembly and the seal assembly are disposed within the recess of the gimbal base.

13. The instrument valve housing of claim 11, wherein the gimbal base includes a shelf, the guard assembly and the seal assembly being disposed between the shelf and the gimbal retainer.

14. The instrument valve housing of claim 13, wherein at least one of the gimbal retainer or gimbal base includes a plurality of pins and at least one of the gimbal retainer or the gimbal base defines a plurality of openings corresponding to the plurality of pins.

15. The instrument valve housing of claim 8, wherein the seal assembly includes four seal sections.

16. A valve assembly comprising:
a guard assembly;
a seal assembly disposed adjacent to the guard assembly, the seal assembly having a plurality of seal sections arranged circumferentially around a longitudinal axis of the valve assembly and collectively forming an aperture having a non-continuous circumference; and
a gimbal mount assembly supporting the guard assembly and the seal assembly, the gimbal mount assembly including an outer semispherical surface and an inner surface, the outer semispherical surface of the gimbal mount assembly being in operable engagement with an inner surface of a lower housing section of an instrument valve housing and the inner surface of the gimbal mount assembly being in operable engagement with an outward facing surface of an upper housing section of the instrument valve housing, wherein the gimbal mount assembly is configured to permit angulation of the valve assembly relative to the instrument valve housing.

17. The valve assembly of claim 16, wherein the gimbal mount assembly includes a gimbal base and a gimbal retainer.

18. The valve assembly of claim 17, wherein the gimbal base includes the semispherical outer surface and the gimbal retainer includes the inner surface.

19. The valve assembly of claim 17, wherein the gimbal base defines a recess, the gimbal retainer being securely received within the recess.

20. The surgical access assembly of claim 19, wherein the guard assembly and the seal assembly are disposed within the recess of the gimbal base.

\* \* \* \* \*